(12) United States Patent
Sauer et al.

(10) Patent No.: US 9,561,092 B2
(45) Date of Patent: Feb. 7, 2017

(54) ATTACHMENT FOR AN ORAL HYGIENE DEVICE

(75) Inventors: Michael Sauer, Bad Camberg (DE); Oliver Greve, Kelkheim (DE)

(73) Assignee: BRAUN GMBH, Kronberg (DE)

( * ) Notice: Subject to any disclaimer, the term of this patent is extended or adjusted under 35 U.S.C. 154(b) by 496 days.

(21) Appl. No.: 13/356,831

(22) Filed: Jan. 24, 2012

(65) Prior Publication Data

US 2013/0134062 A1 May 30, 2013

(30) Foreign Application Priority Data

Nov. 25, 2011 (EP) ..................................... 11000558

(51) Int. Cl.
*A61C 17/22* (2006.01)

(52) U.S. Cl.
CPC ............ *A61C 17/222* (2013.01); *A61C 17/225* (2013.01); *A61C 17/22* (2013.01)

(58) Field of Classification Search
CPC ..... A61C 17/22; A61C 17/222; A61C 17/225; A61C 15/047
USPC ........... 15/22.1, 22.2, 22.4, 23, 28; 132/322; 433/114, 115, 118, 131; 601/142; 606/161
See application file for complete search history.

(56) References Cited

U.S. PATENT DOCUMENTS

| | | | | |
|---|---|---|---|---|
| 2,628,377 | A * | 2/1953 | Cockriel | 15/23 |
| 4,235,253 | A * | 11/1980 | Moore | 132/322 |
| 5,209,658 | A * | 5/1993 | Brahler | 433/125 |
| 6,367,108 | B1 | 4/2002 | Fritsch et al. | |
| 6,422,867 | B2 * | 7/2002 | Lang et al. | 433/118 |
| 7,784,138 | B2 * | 8/2010 | Spooner | 15/22.2 |
| 7,836,538 | B2 * | 11/2010 | Cobabe et al. | 15/28 |
| 8,136,192 | B2 * | 3/2012 | Harrison et al. | 15/4 |
| 2009/0019649 | A1 * | 1/2009 | Dickie | 15/22.1 |
| 2009/0162811 | A1 | 6/2009 | Chronister et al. | |

FOREIGN PATENT DOCUMENTS

WO WO 2009/036462 A2 3/2009

OTHER PUBLICATIONS

International Search Report for PCT/IB2012/050352—dated Feb. 21, 2012.
European Search Repor—dated Jul. 1, 2011.

* cited by examiner

*Primary Examiner* — Mark Spisich
(74) *Attorney, Agent, or Firm* — Vladimir Vitenberg (57) ABSTRACT

An attachment for an oral hygiene device is disclosed. The attachment includes a housing; a shaft element movably arranged within the housing and arranged for being coupled to a drive shaft of a handle of the oral hygiene device; and a flexible sealing element attached to the shaft element. The flexible sealing element is arranged to seal a cavity within the attachment intended for accommodating at least a part of the drive shaft in an attached state.

10 Claims, 8 Drawing Sheets

ATTACHMENT FOR AN ORAL HYGIENE DEVICE

CROSS REFERENCE TO RELATED APPLICATIONS

This application claims the benefit of European Patent Convention Application No. 11000558.4, filed Jan. 25, 2011, the substance of which is incorporated by reference in its entirety herein.

FIELD OF THE INVENTION

The present disclosure is directed to an attachment for an oral hygiene device. More particularly, the present disclosure is directed to an oral hygiene device including such an attachment.

BACKGROUND OF THE INVENTION

It is known that oral hygiene devices such as electric toothbrushes are sealed against water entering the interior part of the handle of the electric toothbrush. Nevertheless, some parts such as the drive shaft that extends from an end of the handle may not be sealed when the oral hygiene is used; further the handle itself is also not sealed. This may lead to contamination of the drive shaft and the handle with liquids containing germs such as saliva (mixed with debris removed from the oral cavity) and with bacteria present on the skin of a user.

It is a desire to provide an attachment for an oral hygiene device and an oral hygiene device that are improved over the known attachments and oral hygiene devices.

SUMMARY OF THE INVENTION

In one embodiment, an oral hygiene device is provided. The attachment includes a housing; a shaft element movably arranged within the housing and arranged for being coupled to a drive shaft of a handle of the oral hygiene device; and a flexible sealing element attached to the shaft element. The flexible sealing element is arranged to seal a cavity within the attachment intended for accommodating at least a part of the drive shaft in an attached state.

In another embodiment, a pouch for an oral hygiene device is provided. The pouch includes a pouch body for covering at least a handle of the oral hygiene device. The pouch has at least a sealable opening for receiving the handle and a second opening through which at least a drive shaft of the handle can extend when the pouch is covering the handle. According to a further aspect there is provided an oral hygiene device including an attachment as proposed and a handle.

According to yet another aspect there is provided a kit including at least an attachment as proposed and a pouch as proposed.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, an oral hygiene device includes an attachment and a handle. In accordance with at least one aspect, an attachment for an oral hygiene device is provided that includes a flexible sealing element, which connects a shaft element that is movably mounted inside of a housing of the attachment with the housing. Here, connection with the housing means either a direct connection or a connection with a further insert element that is fixedly mounted at the housing and can thus be considered as an integral part of the housing. The flexible sealing element may in particular be realized as a flexible sealing membrane, which extends between the shaft element and the housing such that the housing is liquid-tightly separated into two partial cavities. The flexible sealing element (or membrane) may in particular be structured, for example, may include structures that compensate for expansion or torsion of the flexible sealing element. The flexible sealing element may in particular cover 360 degree angular range between the shaft element arranged inside the housing and the housing itself in order to provide the sealing function. The shaft element may in particular extend in a longitudinal direction as well as the housing may extend in a longitudinal direction, while the flexible sealing element than liquid-tightly separates the hollow in the housing into two cavities that are arranged successively in longitudinal direction.

During operation, the shaft element is intended to perform a relative motion (in particular a repetitive motion such as an oscillatory rotation or a linear vibration) with respect to the housing. Thus, the flexible sealing element may be arranged to withstand that it is coupled to a moving element and a static element, for example, by having the above mentioned compensation structures or by general elastic and dimensional properties such that the deformation and/or stretching/expansion of the flexible sealing element between the peak motion positions is enabled.

In some embodiments, the flexible sealing element may be arranged to withstand maximum twists (between the shaft element and the housing or insert element) of for example, about ±30 degrees around the longitudinal axis with respect to a rest position, in another embodiment about ±25 degrees, in another embodiment ±22 degrees, in another embodiment about ±20 degrees, in another embodiment about ±18 degrees, in another embodiment about ±16 degrees, or in another embodiment about ±10 degrees at least for a period of about two minutes or about three minutes or about four minutes at an oscillation frequency of between about 30 Hz to about 300 Hz. The flexible sealing element may therefore be equipped with at least one or more longitudinal rip-like structures and/or a bellows structure. In some other embodiments, the flexible sealing element may be arranged to withstand a linear vibration (in particular along the longitudinal extension direction) having peak amplitudes of between about ±0.1 mm to about ±1.0 mm between the shaft element and the housing or insert element at least for a period of about two minutes or about three minutes or about four minutes at an oscillation frequency of between about 30 Hz to about 300 Hz. The flexible sealing element may seal a cavity that is defined at least partly by the flexible sealing element, the shaft element and the housing (or the insert element) against soiling by externally applied liquids.

The flexible sealing element may generally be made from an elastic material such as natural or artificial rubber or an elastomer or a thermoplastic elastomer (TPE). The shaft element and/or the housing or the insert element may be made from a hard plastic material such as PP (polypropylene) or ASA (acrylonitrile styrene acrylate) or any other suitable hard plastic material or other hard material such as metal. In some embodiments, the shaft element, the flexible sealing element and the housing or the insert part may be manufactured in a two-component or multi-component plastic injection molding process. In some embodiments, the flexible sealing element and the shaft element and/or the housing or insert element may be connected by material engagement such as a chemical material bond.

Figure 1:
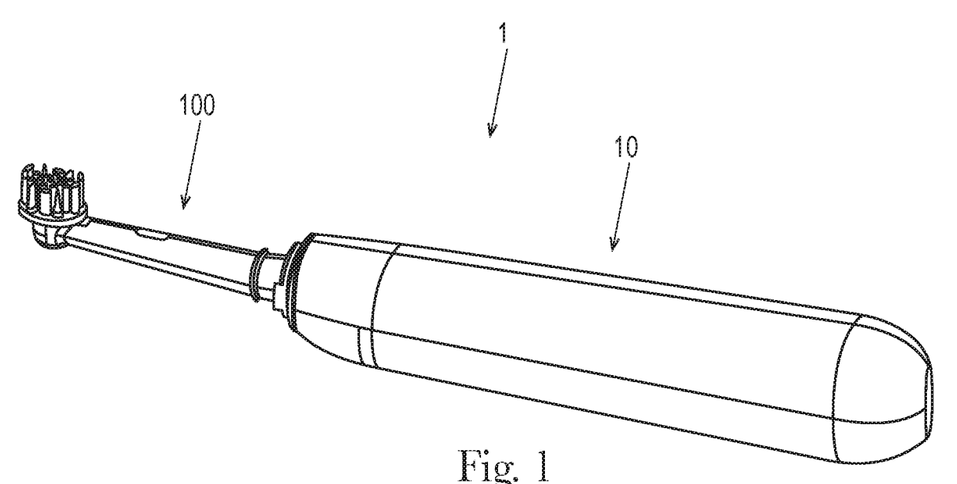
FIG. 1 shows an example oral hygiene device including an attachment.

FIG. 1 is a perspective view onto an example embodiment of an oral hygiene device 1 as proposed in accordance with an aspect of the present disclosure. The oral hygiene device 1 includes a handle 10 and an attachment 100. In one embodiment, the oral hygiene device 1 may be an electric toothbrush and the attachment may be a detachable replacement brush. In other embodiments, the oral hygiene device may be a an electric tongue scraper, an electric flossing device, or an electric gum massaging device.

Figure 2:
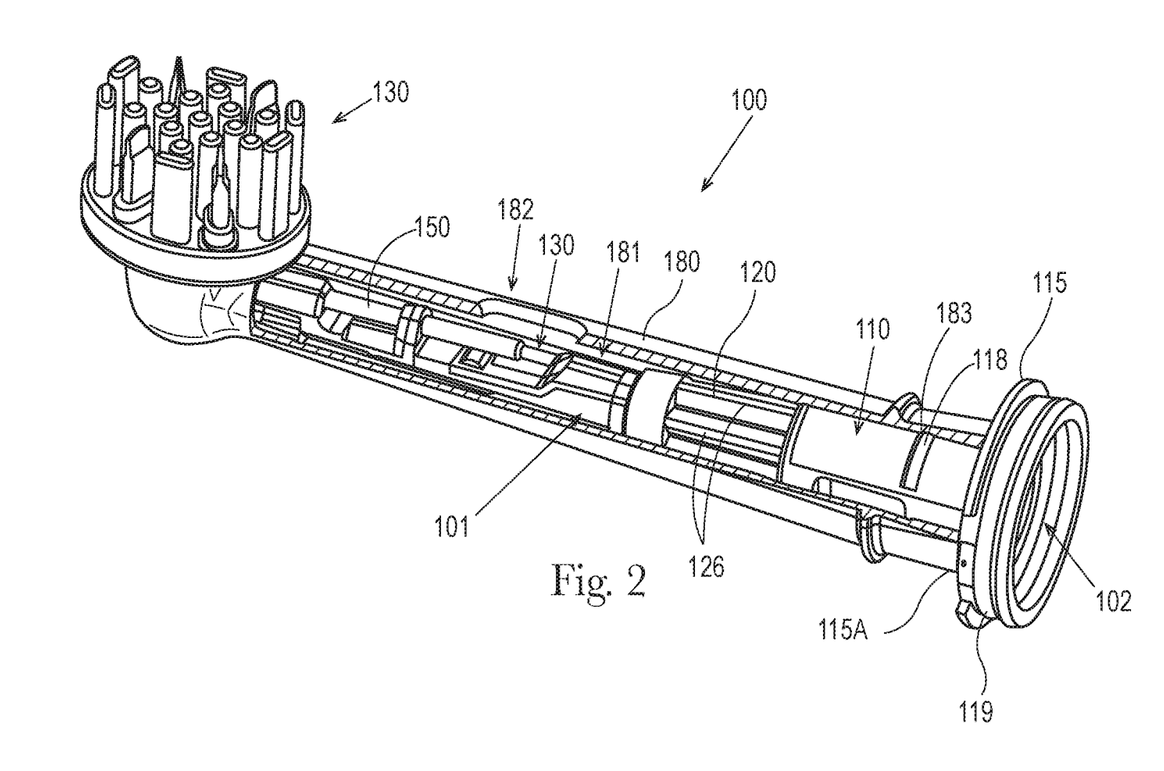
FIG. 2 is a perspective view of an example embodiment of a partly cut-open attachment as proposed.
Figure 3:
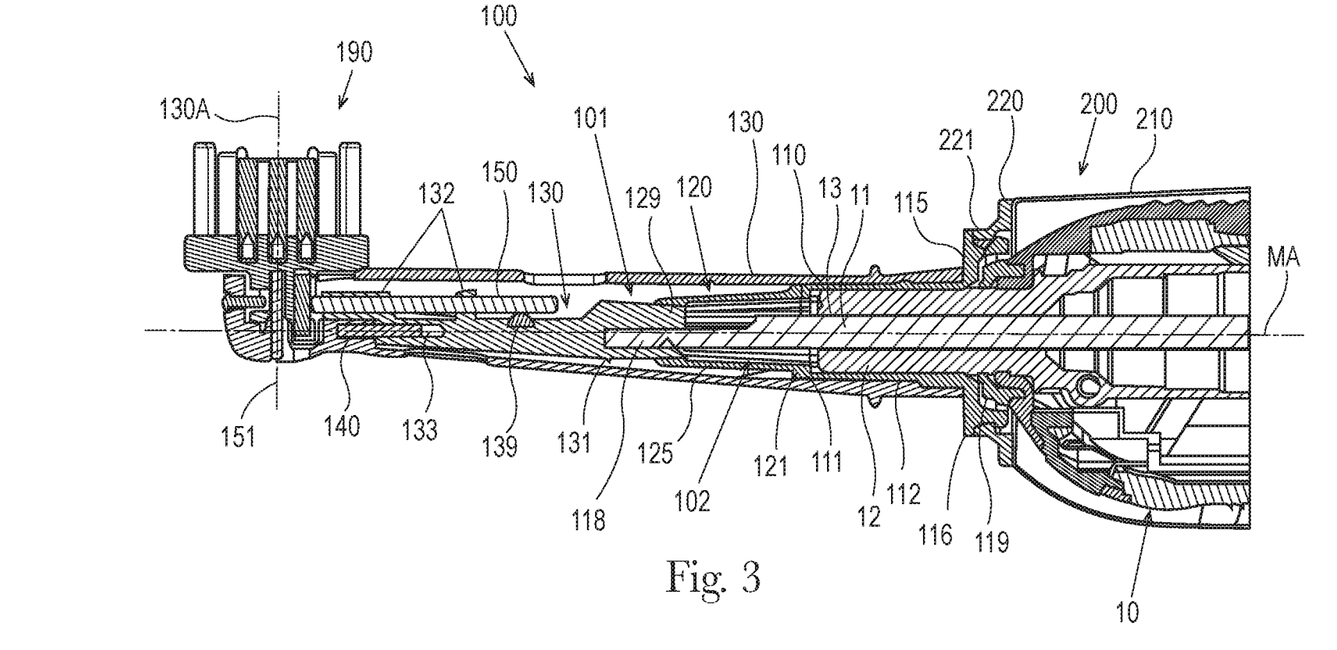
FIG. 3 is a center longitudinal cut through an example embodiment of an oral hygiene device including an attachment as proposed that is attached to a handle (the handle is only partly shown)

FIG. 2 is a perspective view onto an example embodiment of a partly cut-open attachment 100 as proposed in accordance with an aspect of the present disclosure, where the attachment 100 may be a detachable replacement brush intended for attachment to a handle of an electric toothbrush (FIG. 3 shows a longitudinal cut through the attachment shown in FIG. 2 and an upper part of a handle of an oral hygiene device in the attached state). In other embodiments, the attachment may be, for example, a replaceable flossing attachment, a replaceable tongue scraper, or a replaceable gum massaging attachment. The attachment 100 includes an oral cleaning unit 190 that is mounted such that it can be driven into an oscillatory rotation around its centre axis during operation in the attached state. In one embodiment, the oral cleaning unit 190 may be a brush head including bristle tufts and pivoting elastomeric elements for cleaning teeth and stimulating the gums. Other example embodiments of oral care units such as flossing units, tongue scraping units or gum massaging units may be contemplated. Other kinds of—in particular oscillating—movements of the oral cleaning unit may also be contemplated. In particular, the oral cleaning unit may be driven into a linearly oscillating movement, an oscillating poking movement or into a combination of two or more of these movements.

The attachment 100 has a hollow (here: tubular) housing 180 that extends in a longitudinal direction between an end of the attachment distal to the oral cleaning unit 190 and an end proximal to where the oral cleaning unit 190 is mounted. The housing 180 has an aperture 182 through which germ comprising liquids such as saliva (which may in particular contain debris removed from the oral cavity) can enter into the hollow 181 of the housing 180 during use of the attachment 100 in an oral hygiene event, for example, during tooth brushing (the attachment 100 may alternatively or additionally include further openings, for example, where the oral cleaning unit 190 is mounted, through which germ containing liquids can enter into the hollow 181). A coupling structure 115, for example, a ring-like coupling structure that radially projects outwards at the distal end of the attachment 100, is arranged around an opening of a cavity 102 that is intended to receive at least a part of a drive shaft of a handle of an oral hygiene device. An integral part 101 is arranged in the hollow 181 of the housing 180, which integral part 101 generally extends in the longitudinal direction. The integral part 101 includes an insert part 110 (which here is integral with the coupling structure 115), further a flexible sealing element 120 and a shaft element 130. The coupling structure 115 includes a sealing element 119 for establishing a sealed (i.e. liquid tight) connection with a respective coupling partner.

Optionally, a cut-out 115A may be provided in the coupling structure 115 so that a lock-and-key feature can be established. The flexible sealing element 120 is on a first side attached to the shaft element 130 and on a second side attached to the insert part 110. The insert part 110 has a rib 112 that party extends around the insert part 110 and projects radially outwards. The rib 112 mates with a respective recess 183 in the housing 180 so that the insert part 110 is essentially non-movably (i.e. fixedly) mounted at the housing 180. The shaft element 130 is movably mounted at the housing 180 such that it can oscillate around the longitudinal axis that is defined by a rotation axis of the drive shaft of the handle in the attached state during operation. An actuation element 150 (here realized as a metal pin) is mounted at the shaft element 130 and is coupled to the oral cleaning unit 190 such that the oral cleaning unit 190 is driven into an oscillatory rotation around its centre axis when the shaft element 130 is driven into an oscillatory rotation around the longitudinal axis by the drive shaft during operation in the attached state.

In accordance with another embodiment, the drive shaft will provide a longitudinal oscillation (i.e. a linear oscillation in the longitudinal direction). The flexible sealing element 120 (which may be realized as a structured foil or as an injection molded membrane etc.) here includes longitudinally extending rib structures 126 that are designed such that the flexible sealing element 120 can compensate that it gets twisted when the shaft element 130 oscillates around the longitudinal axis during operation while the insert part 110 is fixed in its position with respect to the attachment housing 180 (in other words, the cross section of the flexible sealing element 120 in its central region is star shaped and the thickness of the flexible sealing element in such a cross section may be essentially constant). As will be explained in more detail further below, the flexible sealing element 120 is hollow and thus surrounds a part of the cavity 102 for receiving a part of the drive shaft of the handle. Thus, the cavity 102 is sealed against the hollow 181 in the hollow housing 180 and any contaminated liquid that may enter into the hollow 181 can essentially not enter into the cavity 102 as long as the flexible sealing element 120 is intact. The flexible sealing element 120 may be made from an elastic material such as (artificial or natural) rubber or a thermoplastic elastomer (TPE).

FIG. 3 is a center longitudinal cut through an oral hygiene device with an attachment 100 as shown in FIG. 2 being coupled to a handle 10 (the handle 10 is only partly shown). The handle 10 has a drive shaft 11 that extends out of the handle 10. A neck section 12 extending from the handle housing surrounds the drive shaft 11 for a certain length. The insert part 110 and the neck section 12 may be designed so as to positively fit into each other. The drive shaft 11 is coupled to a drive unit disposed within the handle so that it can be driven into an oscillatory rotation around a longitudinal axis 11A. The neck section 12 of the handle 10 and the extending portion of the drive shaft 11 are disposed in the shown attached state in the cavity 102 of the attachment 100. The cavity 102 is defined by the hollow insert part 110, the hollow flexible sealing element 120 and the partly hollow shaft element 130. The flexible sealing element 120 is on a first side attached to the shaft element 130 via a connector structure 129 that encloses the shaft element 130 so as to form a watertight connection. The flexible sealing element 120 is on a second side attached to the insert part 110 via a connector structure 121 that is connected to a ring-like front face 111 of the insert part 110 so as to form a watertight connection. The integral part 101 including shaft element 130, flexible sealing element 120, and insert part 110 may be manufactured as a two-component (or multi-component) plastic injection molding part. In a first step the insert part 110 and the shaft element 130 may be made from a hard plastic material such as PP (polypropylene) or ASA (acrylonitrile styrene acrylate) either in a single cavity or in two separate cavities and in a second step, the flexible sealing element 120 may be injection molded onto the insert part 110 and the shaft element 130 using a soft thermoplastic material such a thermoplastic elastomer (TPE). The hard plastic material and the thermoplastic material may in particular be chosen such that they enter into a watertight material bond at the connection surfaces. In an embodiment, the shaft element and/or the insert part may be made from a reinforced plastic material, for example, a glass fiber reinforced PP. In another embodiment, the flexible sealing element is made from a rubber foil and is glued to the insert part and the shaft element.

Generally it is to be stated that the flexible sealing element may in another embodiment be attached to a shaft element and may be further attached to, for example, the housing of the attachment to thus seal the cavity against liquid. The insert part as shown in the example embodiments allows for relatively easy mounting of the parts whereas a direct attachment of the flexible sealing element to a part of the housing does not require as many separate parts as in the shown example embodiment. Further, the coupling structure 115 (being an optional feature) may be realized integral with the housing.

In the shown example embodiment, the drive shaft 11 has a flat front part 11B (which means that the front part has a non-circular cross section) that positively fits—essentially playfree—with a coupling section 131 of the shaft element 130 (which coupling section 131 is here a recess in the shaft element 130 and forms a part of the cavity 102). Hence, when the drive shaft 11 is driven into an oscillatory rotation around the longitudinal axis 11A by the drive unit during operation, the drive shaft 11 then takes along the shaft element 130 and the shaft element follows the movement of the drive shaft around the longitudinal axis 11A. The shaft element 130 is mounted at the housing 180 via a mounting element 140 (which may be realized as a metal mounting pin), which mounting element 140 extends along the longitudinal axis 11A such that oscillatory rotation of the shaft element 130 around the longitudinal axis 11A is enabled when the drive shaft 11 takes along the shaft element 130. An actuation element 150 (which may be realized as a metal actuation pin) is mounted at the shaft element 130 at mounting bores 132 so as to be movable in longitudinal direction (i.e. along an actuation element axis that is parallel to the longitudinal axis 11A). A coupling element 151 is coupled to the actuation element 150 (for example, the coupling element may be realized as a metal pin that is welded to the actuation element 150 so that a T-like actuation-coupling-structure results) and sits in a transverse bore in a carrier structure of the oral cleaning unit 190. When the shaft element 130 oscillates around the longitudinal axis 11A, then the eccentrically mounted actuation element 150 moves along a circular segment and thereby oscillates the oral cleaning section 190 around its center axis 190A. During the oscillation, the actuation element 150 slightly moves along the longitudinal direction. A stopper element 139 made from an elastomeric material may be in contact with the actuation element 150 and whenever the drive shaft is not moved, then the stopper element 139 essentially inhibits a free movement of the actuation element 150 due to friction between the actuation element 150 and the stopper element 139 and clattering noises generated by an otherwise freely movable attachment in a non-driven state are reduced.

In accordance with an aspect of the present disclosure, the stopper element 139 may be considered as a feature of individual value. Hence, in accordance with this aspect, an attachment for an oral hygiene device is provided that includes at least a movable actuation element that is in frictional contact with a stopper element to reduce free motion of the movable actuation element in a non-driven state. Any other feature as discussed in the present disclosure may be individually combined with this aspect.

In the example embodiment shown in FIG. 3, the insert part 101 is integral with a coupling structure 115 that radially extends around the end of the attachment 100 proximal the handle 10 in the attached state. The coupling structure 115 here includes a negative snap-ring structure 116 that mates with a respective positive snap-ring structure 221 of a coupling structure 220 of a pouch 200. A sealing element 119 is here provided in the negative snap-ring structure 116 such that the mated snap-ring structures 116 and 221 form a watertight connection. The sealing element 119 may be realized by an O-ring or the sealing element 119 may be an injection molded part. The pouch 200 includes a pouch body 210 that may be realized as a thin plastic foil (for example, made from polyester) that may be transparent. The pouch body 210 is attached to the coupling structure 220 in a watertight manner. The pouch 200 may fully enclose the handle 10 while it allows for undisturbed operation (for example, pushing of an on/off button etc.) of the handle 10 by a user during operation. In an embodiment, the pouch 200 has a further sealable opening at the other end (not shown) and the pouch body 210 is dimensioned to completely accommodate the handle 10. In use, the user may first couple the pouch on one end to the attachment and then slide the handle into the pouch 200 via the sealable opening at its other end until the drive shaft enters the cavity in the attachment and couples with the shaft element. Then the user may seal the sealable end of the pouch body and can use the oral hygiene device essentially without fear of contaminating any part of the handle. A sanitizing step may thus not be necessary after use if the handle is to be used by several users, for example, during a clinical test, but the next user just uses its own attachment and pouch. The pouch 200 may include a sanitary coating such as an antimicrobial coating on its inner and/or on its outer surface.

As has been said before, the flexible sealing member 120 is utilized to seal the cavity 102 (i.e. the drive shaft 11 and also the neck section 12 when the attachment 100 is attached to the handle 10) against contamination by germs (bacteria etc.) during operation. In particular, as can be seen in the example embodiment shown in FIG. 3, a gap 13 may exist between the drive shaft 11 and the neck section 12 such that contaminated liquids may enter into this gap 13. The gap 13 is particularly hard to clean and sanitizing the handle 10 after use may not be simply possible. The pouch 200 has a twofold function. It envelopes and thus effectively seals the whole handle 10 against contamination by germs or bacteria that may be present on the skin of the hand of a user. Further, as the pouch 200 is also coupled to the attachment 100 in a watertight manner (and thus may be considered to form a part of the attachment), any liquids (for example, saliva) including germs or bacteria are efficiently inhibited to enter the cavity 102 from the side of the handle 10. In another embodiment, a sealing structure may be arranged at the attachment such that it seals the attachment against the handle in the attached state. In another embodiment, the pouch may be directly connected to the attachment (for example, by gluing)

It is to be noted that the example embodiment shown in FIGS. 2 and 3 shows several features that are optional with respect to an aspect of the present disclosure. According to this aspect, a movably arranged shaft element (which may be integral with an oral hygiene unit) is arranged, which shaft element is coupled to a drive shaft of a handle of an oral hygiene device in the attached state, and a flexible sealing element seals a cavity accommodating at least a part of the drive shaft between the shaft element and a part of the attachment, where the shaft element will perform a repetitive (in particular: oscillating) motion relative to the part of the attachment during operation (which does not mean that the attachment itself would be necessarily fixed relative to the handle but only that the flexible sealing element is arranged between two parts that will perform relative motion during operation). All other features may individually (where appropriate) or in arbitrary combination be added.

Figure 4A:
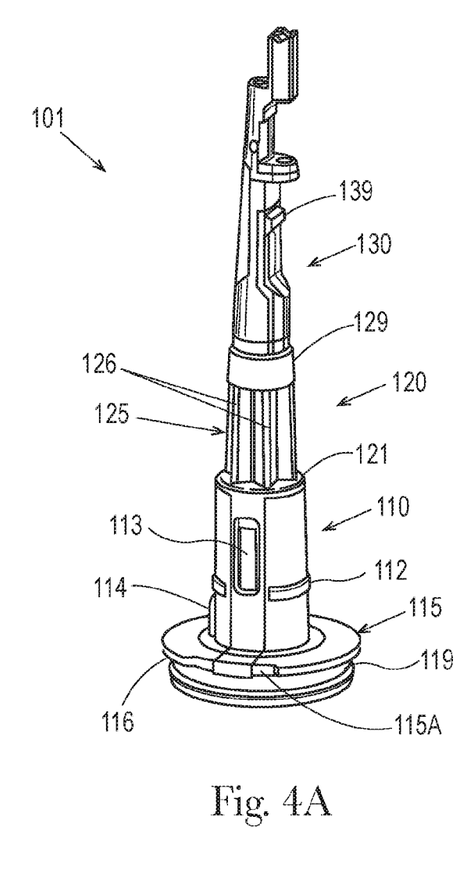
FIG. 4A is a perspective view onto an integral part consisting of a shaft element intended for oscillation around its longitudinal axis, a flexible sealing element and an insert part intended for non-movable mounting to a housing of an attachment according to embodiments shown and described herein.
Figure 5:
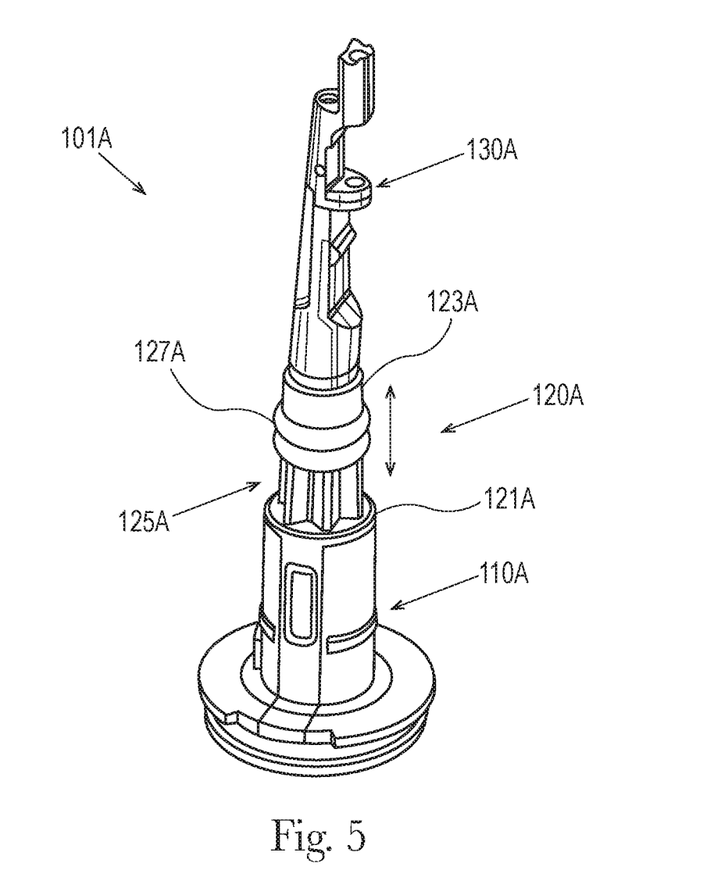
FIG. 5 is a perspective view onto an integral part consisting of a shaft element intended for oscillation around its longitudinal axis and for linear oscillation along the longitudinal axis, a flexible sealing element and an insert part intended for non-movable mounting to a housing of an attachment according to embodiments shown and described herein.

FIG. 4A is a perspective view onto the integral part 101 as discussed with respect to the example embodiment shown in FIGS. 2 and 3. The integral part 101 may be manufactured using two-component (or multi-component) plastic injection molding technology as was explained above. The integral part 101 includes an insert part 110 that may—as shown here—be integral with a radially outwards extending ring-like coupling structure 115, a flexible sealing element 120, and a shaft element 130. The flexible sealing element 120 may be attached to the shaft element 130 to a ring-shaped surface that encircles the shaft element 130 by a connector structure 129 and may be attached to the insert part 110 along a front face of the integral part via a connector structure 121. A central portion 125 extends between the two connector structures 129 and 121. The central portion 125 has here longitudinally extending ribs 126 to enhance the ability of the flexible sealing element 120 to withstand maximum twists of for example, about ±30 degrees around the longitudinal axis with respect to a rest position, in another embodiment about ±25 degrees, in another embodiment about ±22 degrees, in another embodiment about ±20 degrees, in another embodiment about ±18 degrees, in another embodiment about ±16 degrees, or in another embodiment about ±10 degrees at least for a period of about two minutes or about three minutes or about four minutes at an oscillation frequency of between about 30 Hz to about 300 Hz. In another embodiment, where the drive shaft linearly oscillates, the flexible sealing element may be arranged to withstand longitudinal expansions and contractions of about ±0.1 mm to about ±2 mm around a rest position, in another embodiment of about ±0.5 mm to about ±1.5 mm at an oscillation frequency of about 30 Hz to about 300 Hz. In yet another embodiment, the flexible sealing element may be structured to withstand combinations of twists and longitudinal expansions and contractions (an example embodiment is shown in FIG. 5).

Of course the flexible sealing element 120 may be designed to withstand the repetitive movements during operation for a much longer time period, but in case the attachment is intended for a single use (for example, during a clinical trial) it would be sufficient if the flexible sealing element 120 seals reliably for a time period of a typical oral hygiene event (for example a tooth brushing event).

FEM (finite elements method) simulations may be used to determine the material and the dimensions and geometrical structure of the flexible sealing element such that besides structural integrity it is also ensured that the flexible sealing element does not provide too much resistance such that a breakdown in oscillation angle and/or frequency is essentially avoided to achieve cleaning results and use feeling comparable to a similar attachment without a flexible sealing element. The shaft element 130 may include a stopper element 139 which is here used to provide a resistance against free movement of the actuation pin 150 (shown in FIG. 3) when the device is not in operation. The insert part 110 may include a radially outwards projecting rib 112 for snapping the insert part 110 into a respective recess in the housing of the attachment (this snap connection may be designed to be non-detachable to avoid that the integral part can be easily separated from the housing). The insert part 110 may further include a radially outwards projecting nose 114 to establish a lock-and-key feature to enhance correct positional coupling between the integral part 101 and the housing of the attachment. The housing of the attachment hence may include a respective recess to accommodate the nose 114. Similarly, the coupling structure 115 may include a cut-out 115A to establish a lock-and-key feature. The coupling structure 115 may also include a negative snap-ring structure 116 in which a sealing element 119 is arranged. In addition, the insert part 110 may include a spring element 113 that will be explained in more detail further below.

Figure 4B:
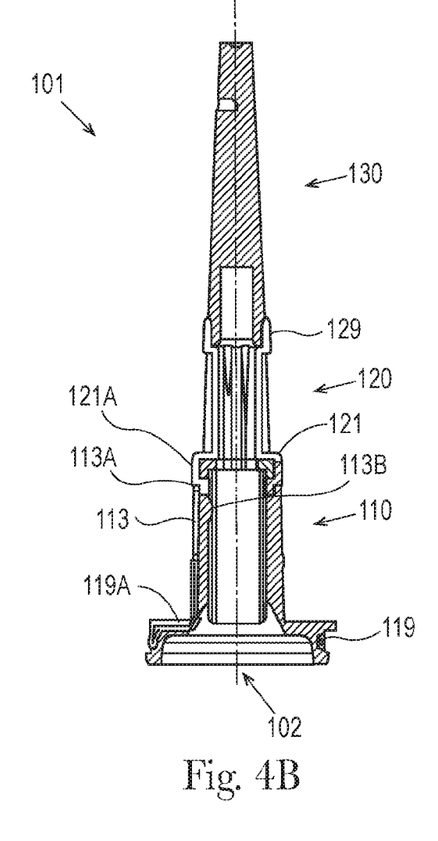
FIG. 4B is a center longitudinal cut through the integral part shown in FIG. 4A, where the cut is taken though a spring element formed in the insert part.

FIG. 4B is a center longitudinal cut through the integral part 101 shown in FIG. 4A, where the cut plane extends through the center of the spring element 113. The spring element 113 may be formed as a tongue element that is integral with the insert part 110 at one end but that is coupled to the insert part 110 at its sides and at its tip via an elastomeric material 113A. The elastomeric material on the one hand seals the spring element 113 against the insert part 110 and on the other hand allows for a certain flexibility of the spring element 113 such that it can for example, pivot outwards. The spring element 113 may include a radially inwards extending projection 113B. When the attachment is attached to the handle, the neck section 12 (as shown in FIG. 3) slides into the part of the cavity 102 formed by the insert part 110. The neck section then forces the spring element 113 to pivot outwards by pushing against the projection 113B. In return, the spring element 113 clamps the attachment to the neck section to inhibit easy separation of the attachment from the handle.

It can be seen in FIG. 4B that the sealing element 119 of the coupling structure 115, the flexible sealing 113A of the spring element 113 and the flexible sealing element 120 may be made in the same injection molding step and that those elastomeric structures may be connected by connecting channels 119A and 121A. The stopper element 139 shown in FIG. 4A may also be made in the same injection molding step from the same thermoplastic material and may be connected to the flexible sealing element 120 by a further connecting channel.

When the integral part 101 is mounted into the housing of the attachment, the mounting element and the actuation element may be mounted to the shaft element 130 and then the integral part may be slid into the hollow of the housing until the mounting element mates with the respective bore in the housing and simultaneously the rib 112 mates with the respective recess in the housing.

FIG. 5 is a perspective view onto a different example embodiment of an integral part 101A similar to the integral part shown in FIG. 4A. Here, the flexible sealing element 120A includes a bellows structure 127A (here realized as a gaiter) that is structured to withstand repetitive linear oscillations of the shaft element 130A with respect to the insert part 110A along the longitudinal axis as indicated by the double arrow L. Linear oscillations around a rest position may have maximum amplitudes of between about ±0.1 mm to about ±2.0 mm. The bellows structure 127A expands and contracts during these oscillations. In the shown embodiment, the bellows structure 127A is realized in addition to a torsion withstanding part 125A of the flexible sealing element 120A; in another embodiment only a bellows structure may be present.

Figure 6:
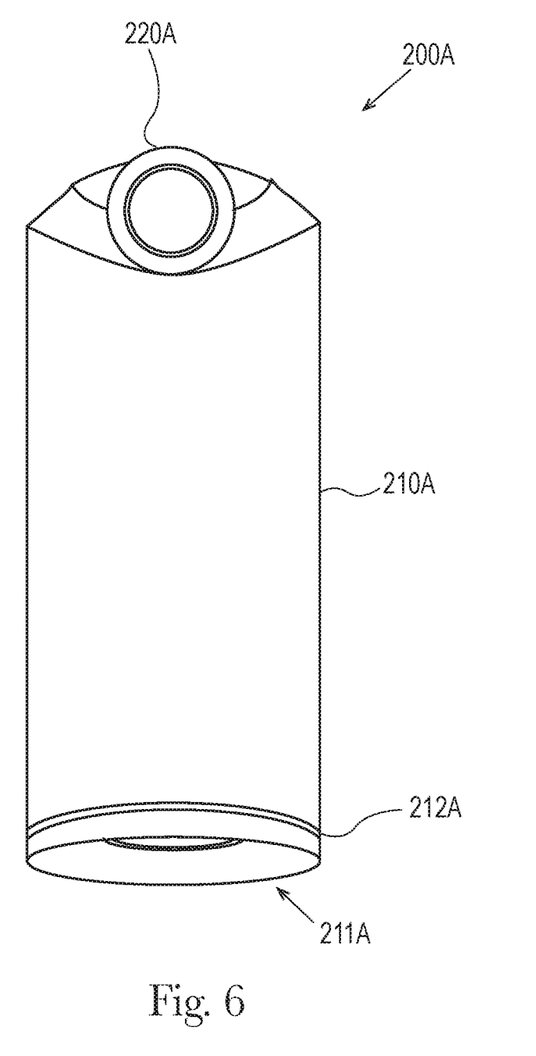
FIG. 6 is a depiction of a pouch according to embodiments shown and described herein.

FIG. 6 is a schematic depiction of an example embodiment of a pouch 200A. In one embodiment, the pouch 200A includes a pouch body 210A (e.g. a (low-density) polyester ((LD)PE) or polypropylene (PP) bag) that has a sealable or re-sealable opening 211A (in one embodiment this may be essentially realized as in a (re-)sealable plastic zip pouch or pressure seal pouch; in another embodiment the sealing may be realized by adhesion, for example, as an adhesive seal pouch) at one end to receive the handle of an oral hygiene device and a connector structure 220A arranged at a second end such that at least a drive shaft of a handle can extend through the connector structure 220A as was explained further above with reference to FIG. 3. In the shown embodiment, a re-sealable closure is achieved by a slide fastener 212A (or: pressure closure). The connector structure 220A is attached to the pouch body 210A by any suitable means, for example, by clamping, gluing or (laser) welding and is intended for connection with a respective connector structure at the attachment.

Figure 7:
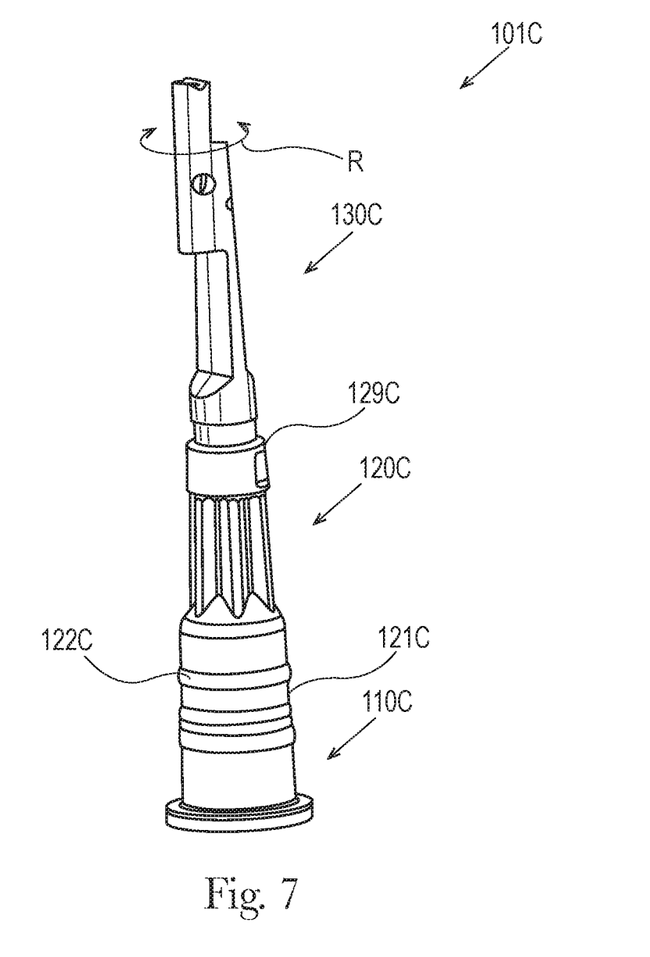
FIG. 7 is a perspective view onto a different embodiment of an integral part.

FIG. 7 is a perspective view onto a further example embodiment of an integral part 101C that includes a shaft element 130C, a flexible sealing element 120C, and an insert element 110C. The shaft element 130C is intended for oscillatory rotation R (indicated by a double arrow) around the longitudinal extension direction relative to the insert element 110C, which insert element 110C is intended to be fixedly mounted into a housing of an attachment (see FIG. 8). The flexible sealing element 120C connects the insert element 110C and the shaft element 130C and is intended to withhold the repetitive relative motion of the shaft element 130C with respect to the insert element 110C during operation. The flexible sealing element 120C may include a ring-like, radially outwards extending sealing structure 122C. The flexible sealing element 120C has a connector structure 121C with which it is connected to insert structure 110C, which connector structure 121C extends as a continuation of the cylindrical insert structure 110C. The connector structure 121C is intended to be in snug contact with the inner wall of a housing of an attachment comprising the integral structure 101C such that by the snug contact a liquid-tight contact is established (as will be discussed with reference to FIG. 8). The flexible sealing element 120C has a further connector structure 129C with which it is connected to the shaft element 130C.

Figure 8:
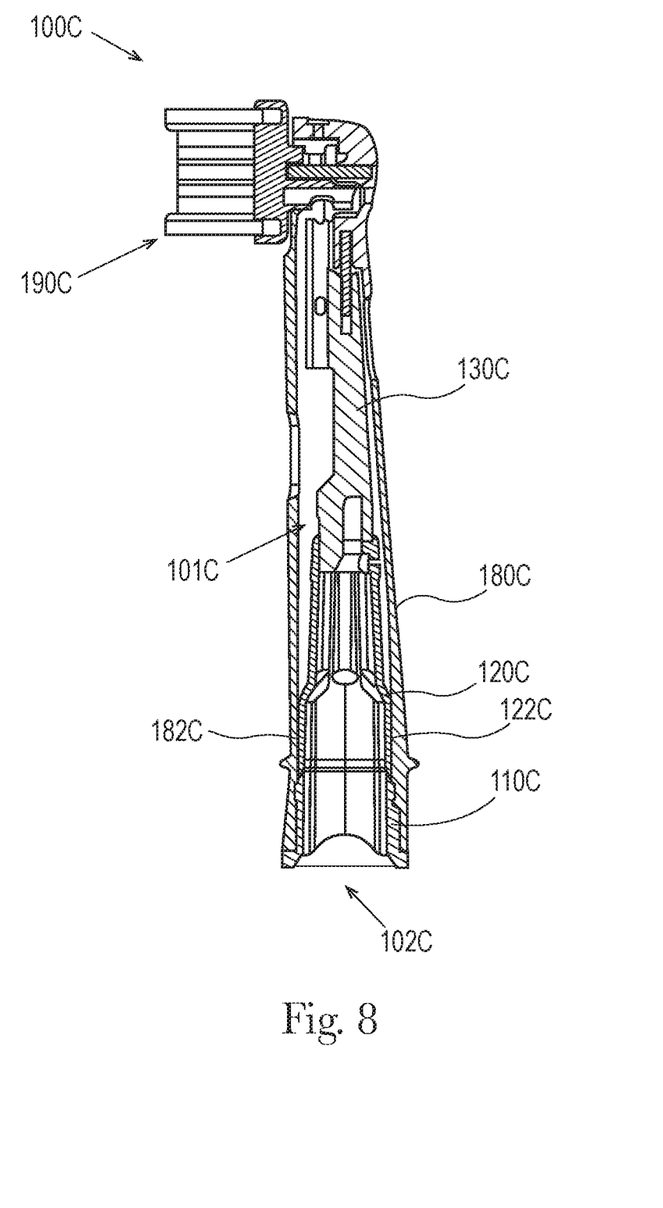
FIG. 8 is a cross sectional cut through an embodiment of a partially assembled attachment for an oral hygiene device including an integral part as shown in FIG. 7.

FIG. 8 shows a cross-sectional cut through an example embodiment of an attachment 100C (only partially assembled) that includes an integral element 101C as shown in FIG. 7. The attachment 100C may include an oral cleaning unit 190C. An insert element 110C is fixedly mounted at a housing 180C of the attachment 100C. A flexible sealing element 120C that is coupled to the insert element 110C by material engagement connects the insert element 110C with a shaft element 130C, which shaft element 130C is movably mounted within the housing 180C. The insert element 110C, the flexible sealing element 120C and the shaft element 120C define a hollow 102C that is intended to receive a drive shaft of a handle of an oral hygiene device as was discussed with reference to FIG. 3.

As was explained above, in an attached state the drive shaft is mechanically coupled to the shaft element 110C and may transfer during operation repetitive motion to the shaft element 130C (in particular oscillatory rotational or linear vibration motion), which shaft element 130C would then perform a relative oscillatory motion with respect to the insert element 110C and thus also with respect to the housing 180C. In some embodiments, the flexible sealing element 120C may be intended to withstand maximum twists of for example, about ±30 degrees around the longitudinal axis with respect to a rest position, in another embodiment about ±25 degrees, in another embodiment about ±22 degrees, in another embodiment about ±20 degrees, in another embodiment about ±18 degrees, in another embodiment about ±16 degrees, or in another embodiment about ±10 degrees at least for a period of about two minutes or about three minutes or about four minutes or about five minutes or about six minutes at an oscillation frequency of between about 30 Hz to about 300 Hz.

In the example embodiment discussed with reference to FIGS. 7 and 8 in particular but also more generally, an additional pouch may not be needed if a neck section of a handle (see FIG. 3) extending into the cavity 102C may snugly fit into this lower portion of the cavity such that the flexible sealing element 120C forms a liquid-tight sealing enclosure. Thus, the drive shaft is effectively protected from soiling during operation. In the example embodiment shown in FIGS. 7 and 8, the ring-like sealing structure 122C may be squeezed into a ring-like groove 182C in the attachment housing to even enhance the liquid-tight sealing function of the flexible sealing element.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An attachment for an oral hygiene device, comprising:
   a housing;
   a shaft element movably arranged within the housing and arranged for being coupled to a drive shaft of a handle of the oral hygiene device for a rotational oscillating movement around a longitudinal axis of the shaft; and
   a flexible sealing element attached to the shaft element, wherein the flexible sealing element is arranged to seal a cavity within the attachment intended for accommodating at least a part of the drive shaft in an attached state, and wherein the flexible sealing element comprises a plurality of longitudinal ribs structured and configured to cause the flexible sealing element to withstand maximum twists of the shaft element during its rotational oscillating movement.

2. The attachment according to claim 1, wherein the flexible sealing element is also attached to the housing and extends approximately 360 degrees between the housing and the shaft element.

3. The attachment according to claim 1, wherein the cavity extends in a longitudinal direction from a proximal end, where the cavity has an opening to receive the drive shaft when being attached to the handle to a distal end that is located within the shaft element.

4. The attachment according to claim 3, wherein the flexible sealing element extends in the longitudinal direction and forms an enclosure of at least a part of the cavity.

5. The attachment according to claim 1, wherein the flexible sealing element is attached to an insert part that is fixedly mounted at the housing.

6. The attachment according to claim 5, wherein the shaft element, the flexible sealing element and the insert part form an integral part.

7. The attachment according to claim 6, wherein the integral part is a two-component or multi-component plastic injection molding part.

8. The attachment according to claim 1, further comprising a movably mounted oral cleaning unit coupled to the shaft element.

9. The attachment according to claim 1, wherein the shaft element is driven in an oscillatory rotation around the longitudinal axis of the attachment with a deflection angle of between about ±5 degrees to about ±30 degrees.

10. The attachment according to claim 1, wherein the maximum twists are selected from the group consisting of twists of about ±30 degrees, twists of about ±25 degrees, twists of about ±22 degrees, twists of about ±20 degrees, twists of about ±18 degrees, twists of about ±16 degrees, and twists of about ±10 degrees around the longitudinal axis of the shaft.

* * * * *